(12) United States Patent
Onodera et al.

(10) Patent No.: US 11,450,489 B2
(45) Date of Patent: Sep. 20, 2022

(54) SMALL ELECTRONIC DEVICE

(71) Applicant: Kyushu Institute of Technology, Kitakyushu (JP)

(72) Inventors: Hideharu Onodera, Chiba (JP); Takahiro Ito, Iizuka (JP)

(73) Assignee: Kyushu Institute of Technology, Fukuoka (JP)

( * ) Notice: Subject to any disclaimer, the term of this patent is extended or adjusted under 35 U.S.C. 154(b) by 825 days.

(21) Appl. No.: 16/061,621

(22) PCT Filed: Nov. 8, 2016

(86) PCT No.: PCT/JP2016/083066
§ 371 (c)(1),
(2) Date: Jun. 12, 2018

(87) PCT Pub. No.: WO2017/104296
PCT Pub. Date: Jun. 22, 2017

(65) Prior Publication Data
US 2020/0143998 A1 May 7, 2020

(30) Foreign Application Priority Data
Dec. 14, 2015 (JP) .............................. JP2015-243020

(51) Int. Cl.
*H01G 11/78* (2013.01)
*H02J 50/10* (2016.01)
(Continued)

(52) U.S. Cl.
CPC ............ *H01G 11/78* (2013.01); *H01G 11/30* (2013.01); *H01M 4/485* (2013.01); *H01M 4/54* (2013.01);
(Continued)

(58) Field of Classification Search
CPC .......... H01G 4/385; H01G 2/10; H01G 2/103; H01G 4/224; H01G 4/232; H01G 4/236;
(Continued)

(56) References Cited

U.S. PATENT DOCUMENTS 4,709,303 A * 11/1987 Fujiwara ................ H01G 9/155
361/502
2007/0106175 A1 5/2007 Uchiyama et al.
(Continued)

FOREIGN PATENT DOCUMENTS

JP 07-302581 A 11/1995
JP 2003-142040 A 5/2003
(Continued)

OTHER PUBLICATIONS

Notice of Allowance dated Jan. 7, 2020 in corresponding Japanese Patent Application No. JP 2015-243020.
(Continued)

*Primary Examiner* — Michael P McFadden
(74) *Attorney, Agent, or Firm* — Mintz Levin Cohn Ferris Glovsky and Popeo, P.C.; Katherine C. Jensen

(57) ABSTRACT

The present invention provides a small electronic device including an actuation component that operates using an electromagnetic force, a power storage device, and a case in which the actuation component and the power storage device are stored, in which the power storage device is formed of a non-magnetic body.

5 Claims, 3 Drawing Sheets

(51) Int. Cl.
   *H01G 11/30*   (2013.01)
   *H01M 4/485*   (2010.01)
   *H01M 4/54*    (2006.01)
   *H01M 50/10*   (2021.01)
   *H01M 50/20*   (2021.01)

(52) U.S. Cl.
   CPC ............. *H01M 50/10* (2021.01); *H02J 50/10* (2016.02); *H01M 50/20* (2021.01)

(58) Field of Classification Search
   CPC . H01G 4/32; H01G 2/24; H01G 5/011; H01G 5/014; H01G 11/78; H01G 11/30; H02J 50/10; H01M 50/10; H01M 4/485; H01M 4/54; H01M 50/20
   See application file for complete search history.

(56) References Cited

U.S. PATENT DOCUMENTS

| | | | |
|---|---|---|---|
| 2007/0290814 A1 | 12/2007 | Yoshida | |
| 2008/0079565 A1 | 4/2008 | Koyama | |
| 2008/0094777 A1* | 4/2008 | Itahashi | H01G 11/62 361/502 |
| 2008/0275430 A1* | 11/2008 | Belsky | A61M 31/002 604/890.1 |
| 2009/0253999 A1* | 10/2009 | Aoki | A61B 1/0005 600/565 |
| 2010/0252314 A1* | 10/2010 | Ashizaki | H01G 11/74 174/260 |
| 2013/0120706 A1 | 5/2013 | Kakinuma et al. | |
| 2014/0378760 A1 | 12/2014 | Ito et al. | |
| 2015/0263335 A1* | 9/2015 | Sugaya | C01G 39/00 429/231.5 |
| 2018/0259914 A1* | 9/2018 | Chae | G04G 17/08 |

FOREIGN PATENT DOCUMENTS

| | | |
|---|---|---|
| JP | 2003-526268 A | 9/2003 |
| JP | 2005-270461 A | 10/2005 |
| JP | 2007-125356 A | 5/2007 |
| JP | 2007-330404 A | 12/2007 |
| JP | 2008-109847 A | 5/2008 |
| JP | 2009-295331 A | 12/2009 |
| JP | 2011-210898 A | 10/2011 |
| JP | 5190108 B2 | 4/2013 |
| JP | 2013-084591 A | 5/2013 |
| JP | 2015-069881 A | 4/2015 |
| JP | 2015-220108 A | 12/2015 |
| WO | 01/65995 A2 | 9/2001 |
| WO | 2014/014062 A1 | 1/2014 |
| WO | 2014/021046 A1 | 2/2014 |

OTHER PUBLICATIONS

International Search Report issued in PCT/JP2016/083066, dated Dec. 20, 2016.
International Preliminary Report on Patentability issued in PCT/JP2016/083066, dated Nov. 14, 2017.
Office Action dated Oct. 23, 2019 in corresponding Japanese Patent Application No. 2015-243020.
Extended European Search Report issued in European Application No. 16875281.4, dated Aug. 21, 2018.

* cited by examiner

SMALL ELECTRONIC DEVICE

TECHNICAL FIELD

The present invention relates to a small electronic device.

BACKGROUND ART

Hitherto, for small electronic devices, commercial power sources, power storage devices, or sunlight has been used as power sources. Examples of power storage devices include primary batteries, secondary batteries, electric double layer capacitors, and the like, and power storage devices are classified into electrifiable devices and non-electrifiable devices. A power source for a small electronic device may be disposed inside the small electronic device or may be disposed outside the small electronic device. In a case in which a small electronic device includes a power source therein, it is possible to use a power storage device as the power source. However, as the size of the power storage device decreases, the capacity decreases, and thus there is a case in which it is not possible to obtain a sufficient actuation time as an electronic device. In a case in which a small electronic device receives power from a power source disposed outside, it is possible to supply power to the small electronic device from a power source having a sufficient amount of power through such as a commercial power source or a large power storage device through a lead wire. However, for example, in small electronic devices that are used in human bodies, it becomes extremely difficult to supply power through a lead wire. In addition, in small electronic devices that are used in the ground, water or the air as well, it is difficult to supply power through a lead wire.

Recently, as a means for supplying power, a wireless power transmission technique has been disclosed (for example, refer to Patent Document 1). When this technique is used, there is a possibility that power can be supplied from power sources disposed outside to devices for which the disposition of lead wires is difficult or devices for which lead wires cause disruption. On the basis of this technique, a variety of transmission methods have been studied, and, at the moment, electromagnetic induction systems, magnetic resonance systems, electric field coupling systems, systems using electric waves, and the like are being studied. These systems are being used appropriately depending on available frequencies or transmission power, transmission efficiencies, transmission distances, and the like. Among them, the systems using magnetic fields are capable of transmitting a relatively large amount of power and thus broadly used. In the system, a coil is provided in each of a power transmission portion and a power-receiving portion, and power is transmitted using a magnetic field generated between the two coils. However, when the locations (distance or angles) of the two coils vary, the amount of power received decreases, and thus the relative locations of the power transmission portion and the power-receiving portion need to be fixed in the case of power transmission. In addition, Patent Document 1 describes that a majority of ordinary materials (including animals, plants, and human beings) are not magnetic, and the ordinary materials and magnetic fields interact to the minimum extent; however, when a material such as metal is present close to the coil, there is a problem in that the amount of power received decreases.

For example, as a small electronic device, a capsule endoscope as disclosed in Patent Document 2 has been put into practical use. The capsule endoscope is a device that is swallowed from the mouth and used to capture an image of the inside of a human body using a camera or an LED, and, as a power source, a coin-like silver oxide battery (primary battery) combined into the capsule is used. The capsule endoscope is moved by the peristaltic motion of the digestive canal, and the inspection duration is set to approximately eight hours from swallow to removal.

Furthermore, in recent years, a self-movable capsule endoscope has been disclosed (for example, refer to Patent Document 3). This capsule endoscope has a self-moving function, and thus there is a possibility that the time necessary for passing a human body becomes as short as one to two hours, the burden on the body of a patient can be alleviated, the endoscope can be controlled to advance or retract from the outside of the human body, and an image of an arbitrary location in the human body can be captured. As methods for making capsule endoscopes to move on their own, there are a method in which alternating current is made to flow in a coil fixed in a capsule, a magnet which is an armature is reciprocally moved, and a capsule endoscope is driven using an inertial force generated by the motion of the armature or an impact force generated when the armature collides with an external wall (a moving magnet system) and a method in which a magnet is fixed, and an electric current is made to flow in a coil, thereby oscillating a coil, and a capsule endoscope is driven using the reaction to the oscillation (a moving coil system). Both of these methods are applied to endoscopes that advance in a certain direction. However, in small and highly functional electronic devices as described above, the amount of power consumed increases. As a result of disposing a silver oxide battery in a capsule and conducting a test, the battery was rapidly consumed, and the capacity was not sufficient. The lack of the capacity of the battery can be solved by increasing the size of the silver oxide battery, which creates a concern that the size of the capsule may increase.

Therefore, it is considered that the lack of power can be solved by transmitting power from an external power transmission coil to a power-receiving coil disposed in the capsule wirelessly. However, the capsule moves in a bendy digestive canal such as a small intestine, and the distance or angles of two coils vary, and thus there is a case in which a disadvantage of a decrease in the amount of power received or the blocking of power transmission is caused. In order to solve the disadvantage, a method in which a power storage device is jointly used, the power storage device is charged when the amount of power received is stable, and an endoscope is driven using power from the power storage device when the amount of power received is not stable is considered. It is considered that this method enables the stable supply of power even when the distance or angles of a power transmission coil and a power-receiving coil change. In a capsule constituted as described above, it is necessary to dispose a magnet which is an armature, a power-receiving coil for receiving power, and a power storage device close to one another.

CITATION LIST

Patent Literature

[Patent Document 1] Japanese Patent No. 5190108
[Patent Document 2] Published Japanese Translation No. 2003-526268
[Patent Document 3] PCT International Publication No. WO2014/014062
[Patent Document 4] Japanese Unexamined Patent Application, First Publication No. H7-302581

[Patent Document 5] Japanese Unexamined Patent Application, First Publication No. 2011-210898

SUMMARY OF INVENTION

Technical Problem

However, in power storage devices of the related art, a material that is attracted to a magnet such as a cold-rolled steel sheet or stainless steel as an exterior as disclosed by Patent Document 4, Patent Document 5, or the like, and furthermore, the magnetic property of an electrode material is also not taken into consideration. As a result of investigation, the present inventors found that all of cylindrical dry batteries (D to AAA-type dry batteries), alkaline batteries (LR), silver oxide batteries (SR), lithium batteries (CR), and electric double layer capacitors that are currently on the market are adsorbed to magnets. Therefore, there is a problem in that, when a power storage device that is attracted to a magnet is disposed close to an armature formed of a magnet, the motion of the armature is hindered, and a sufficient force for driving a capsule cannot be obtained. In addition, there is another problem in that, when a power storage device that is attracted to a magnet is disposed close to a power-receiving coil for wireless power transmission, a decrease in the amount of power received.

Therefore, an object of the present invention is to provide a small electronic device capable of preventing the operation of an actuation component from being hindered by the disposition of a power storage device close to the actuation component that operates using an electromagnetic force. In addition, another object of the present invention is to provide a small electronic device capable of suppressing a decrease in the amount of power received caused by the disposition of a power storage device close to a power-receiving coil for wireless power transmission.

Solution to Problem

The present invention employed the followings in order to solve the above-described problems and achieve the relevant objects.

(1) A small electronic device according to a first aspect of the present invention including an actuation component that operates using an electromagnetic force, a power storage device, and a case in which the actuation component and the power storage device are stored, in which the power storage device is formed of a non-magnetic body.

According to this constitution, the power storage device is formed of a non-magnetic body, and thus it is possible to suppress a magnetic field being varied by the disposition of the power storage device close to the actuation component that operates using an electromagnetic force. Therefore, it is possible to prevent the operation of the actuation component from being hindered by the disposition of the power storage device close to the actuation component.

(2) A small electronic device according to a second aspect of the present invention including a power-receiving coil for wireless power transmission, a power storage device, and a case in which the power-receiving coil and the power storage device are stored, in which the power storage device is formed of a non-magnetic body.

According to this constitution, the power storage device is formed of a non-magnetic body, and thus it is possible to suppress the amount of power received being decreased by the disposition of the power storage device close to the power-receiving coil for wireless power transmission.

(3) A small electronic device according to a third aspect of the present invention including an actuation component that operates using an electromagnetic force, a power-receiving coil for wireless power transmission, a power storage device, and a case in which the actuation component, the power-receiving coil and the power storage device are stored, in which the power storage device is formed of a non-magnetic body.

According to this constitution, the power storage device is formed of a non-magnetic body, and thus it is possible to suppress a magnetic field being varied by the disposition of the power storage device close to the actuation component that operates using an electromagnetic force. Therefore, it is possible to prevent the operation of the actuation component from being hindered by the disposition of the power storage device close to the actuation component. In addition, it is possible to suppress the amount of power received being decreased by the disposition of the power storage device close to the power-receiving coil for wireless power transmission.

(4) In the small electronic device according to (2) or (3), the power storage device may be disposed inside the power-receiving coil.

In this case, a limited space in the case can be effectively used, and it becomes possible to decrease the size of the case. Therefore, it is possible to further decrease the size of the small electronic device.

(5) In the small electronic device according to any one of (1) to (4), the power storage device may include an exterior body formed of non-magnetic stainless steel.

In this case, it is possible to manufacture the exterior body with an easier press work compared with a case in which the exterior body is formed of aluminum for which the press work is difficult, and it is possible to reduce the manufacturing cost. Therefore, it is possible to provide an inexpensive small electronic device.

(6) In the small electronic device according to any one of (1) to (5), a constitution may be employed in which the power storage device includes an exterior body, and a protective film formed of a material including at least one of carbon and aluminum is provided in at least a part of a surface of the exterior body which is in contact with an electrolytic solution of the power storage device.

In this case, it is possible to prevent the exterior body from being corroded by the contact between the exterior body and the electrolytic solution. Therefore, it is possible to suppress the performance deterioration of the power storage device.

(7) In the small electronic device according to any one of (1) to (6), an electrode of the power storage device may include at least one of silver oxide, manganese dioxide, lithium cobaltate, lithium manganate, lithium titanate, zinc, carbon, activated carbon, silicon, silicon monoxide, and lithium as a material.

In this case, it is possible to produce a power storage device having a high capacity which is formed of a non-magnetic body to the small electronic device.

(8) In the small electronic device according to any one of (1) to (7), the power storage device may have a coin shape.

In this case, it is possible to store the power storage device with no void in a cylindrical case. Therefore, it becomes possible to decrease the size of the case and further decrease the size of the small electronic device. In addition, it becomes possible to effectively use the limited space in the case, and it is possible to produce a small electronic device having higher performance.

(9) The small electronic device according to any one of (1) to (8) may be a capsule endoscope.

In this case, the capsule endoscope has a self-moving function, suppresses a decrease in the amount of power received caused by wireless power transmission, and has high performance, and it is possible to alleviate burdens on patients.

Advantageous Effects of Invention

According to the small electronic devices according to the respective aspects of the present invention, it is possible to prevent the operation of the actuation component from being hindered by the disposition of the power storage device close to the actuation component. In addition, it is also possible to suppress a decrease in the amount of power received being decreased by the disposition of the power storage device close to the power-receiving coil for wireless power transmission.

DESCRIPTION OF EMBODIMENTS

Hereinafter, as a preferred embodiment of a small electronic device of the present invention, for example, a capsule endoscope 1 which is swallowed from the mouth of a human being and captures an image of the inside of the human body using a camera or an LED will be described as an example. Meanwhile, the small electronic device is not solely limited to the capsule endoscope, and the present invention can be applied to other small electronic devices including a component that operates using an electromagnetic force, for example, an actuator, a relay, a switch, a speaker, or an earphone.

Figure 1:
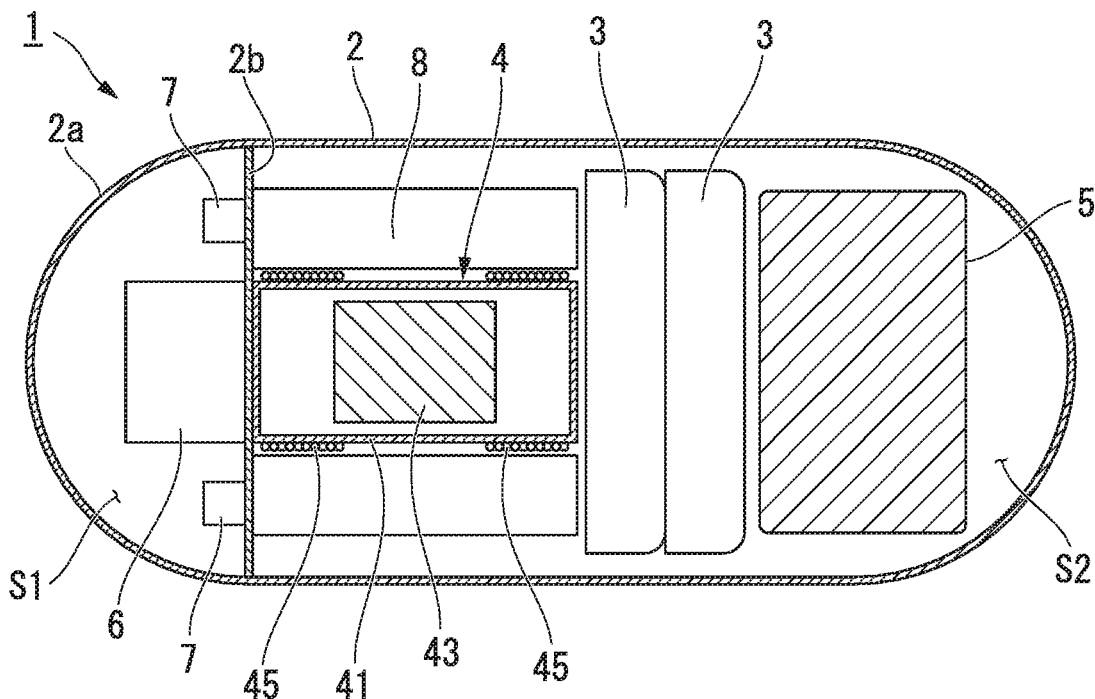
FIG. 1 is a cross-sectional view showing a schematic constitution of a capsule endoscope according to an embodiment of the present invention.

FIG. 1 is a view showing a schematic constitution of a capsule endoscope according to the present embodiment and a cross-sectional view of the capsule endoscope seen on a cross section including a central axis line thereof.

The capsule endoscope 1 is made to be self-movable using the driving force of an actuator 4 (actuation component) described below, includes a small camera or an LED therein, and has a function of capturing an image of the inside of a human body. In more detail, as shown in FIG. 1, the capsule endoscope 1 includes a capsule 2 (case), a pair of power storage devices 3, the actuator 4, a power-receiving coil 5, a camera 6, an LED 7, and a control circuit 8. The pair of power storage devices 3, the actuator 4, the power-receiving coil 5, the camera 6, the LED 7, and the control circuit 8 are disposed inside the capsule 2.

The capsule 2 is made of, for example, a resin material and formed in a cylindrical shape having a hemispherical shape in each of both end portions. One end portion 2a of the capsule 2 is translucent. The capsule 2 is, for example, 11 mm in outer diameter and approximately 26 mm in length. In the capsule 2, a partition wall 2b that divides the inner space into two sections in the axial direction of the capsule 2 (hereinafter, simply referred to as the "axial direction") is provided. The partition wall 2b is provided so as to be orthogonal to the axial direction on the one end portion 2a side of the center in the axial direction. Hereinafter, in the inner space of the capsule 2, the one end portion 2a side of the partition wall 2b will be considered as a first space S1, and the opposite side will be considered as a second space S2.

The pair of power storage devices 3 each have a coin shape and are disposed side by side in the axial direction in the second space S2 in a state in which the power storage devices are connected to each other in series so as to be concentric with the capsule 2. The power storage device 3 supplies power to the actuator 4, the camera 6, the LED 7, and the like through the control circuit 8. The power storage device 3 supplies power from the power-receiving coil 5 through the control circuit 8. The power storage device 3 is formed of a non-magnetic body (a substance that is not a ferromagnetic substance).

Figure 2:
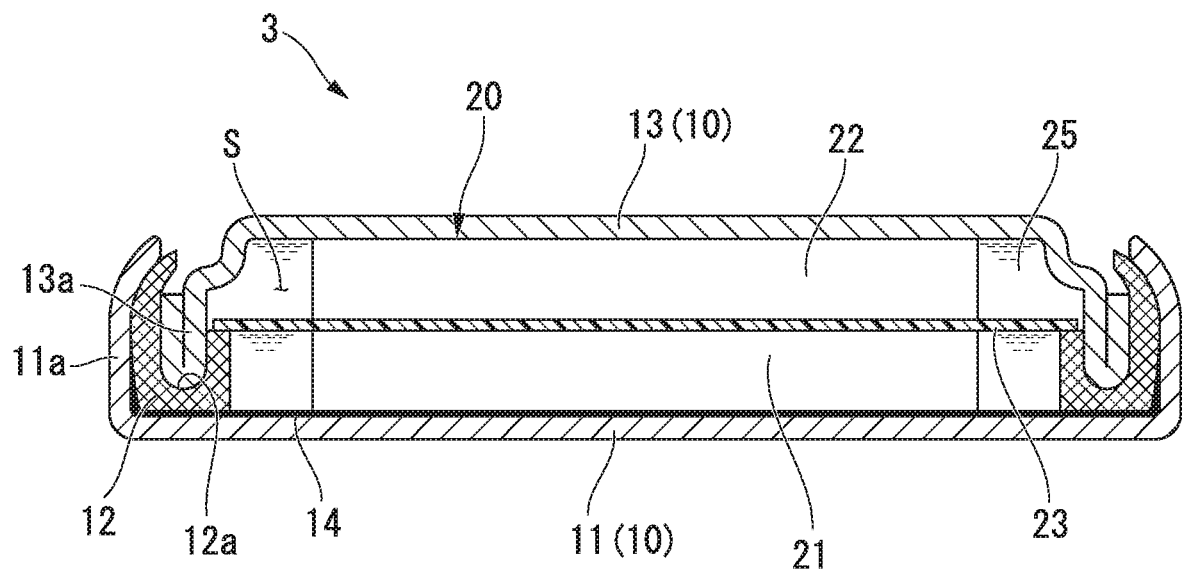
FIG. 2 is a cross-sectional view of a power storage device according to the same embodiment.

FIG. 2 is a view showing the power storage device 3 according to the present embodiment and a cross-sectional view of the power storage device seen on a cross section including an axis line thereof.

As shown in FIG. 2, the power storage device 3 mainly includes an exterior body 10 and an electrode body 20 stored in the exterior body 10 together with an electrolytic solution 25.

The exterior body 10 is formed in a circular shape in a planar view. Specifically speaking, the exterior body 10 has a positive electrode can 11 having a bottomed tubular shape and a negative electrode can 13 having a topped tubular shape which is combined into the positive electrode can 11 through a gasket 12 and defines a storage space S between the positive electrode can 11 and the negative electrode can. In the storage space S, the electrode body 20 and the electrolytic solution 25 are stored. In the example shown in the drawing, the inner diameter of the positive electrode can 11 is larger than the outer diameter of the negative electrode can 13. A protective film 14 is provided on all of a portion of the positive electrode can 11 which faces the storage space S. The protective film 14 prevents the performance deterioration of the power storage device 3 from being accelerated by the corrosion of the positive electrode can 11 caused by the contact with the electrolytic solution 25 in a case in which, particularly, the power storage device 3 is electrifiable. Meanwhile, corrosion by the contact between the positive electrode can 11 and the electrolytic solution 25 is caused during charging, and thus the presence or absence of the protective film 14 does not matter in primary batteries that are not electrifiable.

The gasket 12 is formed in a round shape and fitted into a circumferential wall portion 11a of the positive electrode can 11. A groove portion 12a that holds a circumferential wall portion 13a of the negative electrode can 13 is formed throughout the entire circumference of the gasket 12. The negative electrode can 13 is fixed to the inside of the positive electrode can 11 by swaging the circumferential wall portion 11a of the positive electrode can 11 in a state in which the circumferential wall portion 13a is held in the groove portion 12a of the gasket 12.

The electrode body 20 is formed in a disc shape that matches the inner shape of the exterior body 10. The electrode body 20 includes a positive electrode 21, a negative electrode 22, and a separator 23 interposed between the positive electrode 21 and the negative electrode 22. The positive electrode 21 is laminated on the positive electrode can 11 through the protective film 14 and electrically connected to the positive electrode can 11. The negative electrode 22 is directly laminated on the negative electrode can 13 and electrically connected to the negative electrode can 13.

Hereinafter, materials of the members constituting the power storage device 3 will be described in detail.

First, active materials constituting the positive electrode 21 and the negative electrode 22 of the power storage device 3 will be described. The positive electrode 21 and the negative electrode 22 of the power storage device 3 need to have a sufficient capacity (weight density) and be non-magnetic. The results of investigation on whether or not active materials for a variety of power storage devices having a high capacity are attracted to magnets are shown in Table 1 below.

TABLE 1

| Active material | Magnet test | |
|---|---|---|
| | Powder | Pellet |
| $Ag_2O$ | Good | Good |
| $MnO_2$ | Not Good | Not Good |
| $LiCoO_2$ | Good | Good |
| $Li_4Mn_5O_{12}$ | Not Good | Not Good |
| $Li_4Ti_5O_{12}$ | Good | Good |
| Zn | Good | Good |
| C | Good | Good |
| Activated carbon | Good | Good |
| Si | Not Good | Not Good |
| SiO | Good | Good |
| Li | Good | — |
| Fe (reference) | Very Bad | Very Bad |

In a method for testing of Table 1, a samarium-cobalt magnet having a maximum energy product of 30 MGOe (239 kJ/m$^3$) (manufactured by Seiko Instruments Inc.) was brought into contact with the powder of active materials (a foil only in the case of Li), active materials that were not attracted to the magnet were evaluated as 'Good', active materials that were weakly attracted to the magnet were evaluated as 'Not Good', active materials that were attracted to the magnet were evaluated as 'Bad', and active materials that were strongly attracted to the magnet were evaluated as 'Very Bad'. Fe was evaluated for reference as a representative example of ferromagnetic bodies. In addition, generally, in power storage devices, powder is used in a compressed form in order to increase the capacity per unit volume. Therefore, a specimen obtained by compressing a powder mixture of the active material and a resin binder in a ratio of 9:1 (the active material to the resin binder=9 to 1) with a force of 4 tf/cm$^2$ (392 MPa) to a pellet shape was brought into contact with the magnet in the same manner as described above and evaluated in order to check whether or not the magnetic property varied depending on the plastic deformation of the active material.

In alkaline batteries, $MnO_2$ is used as the positive electrode, and Zn is used as the negative electrode. $MnO_2$ was weakly attracted to the magnet. Zn was not attracted to the magnet.

In silver oxide batteries, $Ag_2O$ is used as the positive electrode, and Zn is used as the negative electrode. Both of $Ag_2O$ and Zn were not attracted to the magnet.

In lithium primary batteries, $MnO_2$ is used as the positive electrode, and Li is used as the negative electrode. $MnO_2$ was weakly attracted to the magnet. Li was not attracted to the magnet.

In lithium secondary batteries, $Li_4Mn_5O_{12}$ or $Li_4Ti_5O_{12}$ is used as the positive electrode. In addition, an active material such as Si or SiO and Li are used in combination as the negative electrode. Among these materials, $Li_4Mn_5O_{12}$ that is used as the positive electrode was weakly attracted to the magnet whereas $Li_4Ti_5O_{12}$ was not attracted to the magnet. In addition, Si that is used as the negative electrode was attracted to the magnet, but SiO was not attracted to the magnet.

In lithium-ion secondary batteries, $LiCoO_2$ is used as the positive electrode, and C is used as the negative electrode. Both of $LiCoO_2$ and C were not attracted to the magnet.

In electric double layer capacitors, activated carbon is used as both the positive electrode and the negative electrode. Activated carbon was not attracted to the magnet.

Meanwhile, for all of the above-described active materials except for Li, the results remained identical both in a powder form and in a pellet form.

Next, the magnetic property of the electrolytic solution in the power storage device will be described. The electrolytic solution 25 in the power storage device 3 needs to be non-magnetic.

In a method for testing the magnetic property of the electrolytic solution, the electrolytic solution was fed into a glass bottle, a magnet was brought close to the electrolytic solution from the outside of the glass bottle, and whether or not the electrolytic solution was attracted was observed.

In alkaline batteries or silver oxide batteries, a sodium hydroxide aqueous solution and a potassium hydroxide aqueous solution are used. Neither the sodium hydroxide aqueous solution nor the potassium hydroxide aqueous solution was attracted to the magnet.

In lithium primary batteries, lithium-ion secondary batteries, and electric double layer capacitors, one or more of the group consisting of propylene carbonate, ethylene carbonate, sulfolane, dimethyl carbonate, diethyl carbonate, ethyl methyl carbonate, dimethoxyethane, and acetonitrile are used as a solvent. The above-described solvents were not attracted to the magnet. As an electrolyte, one or more of the group consisting of lithium perchlorate, lithium borofluoride, lithium hexafluorophosphate, lithium bis(trifluoromethanesulfonyl) imide, lithium bis(fluorosulfonyl) imide, tetraethylammonium fluoroborate, and 5-azoniaspiro (4,4)nonane tetrafluoroborate are used. The above-described electrolytes were not attracted to the magnet. Furthermore, mixtures of the solvent and the electrolyte described above were also not attracted to the magnet.

In addition, 1-ethyl-3-methylimidazolium tetrafluoroborate which is an ionic liquid was not attracted to the magnet. Meanwhile, in recent years, ionic liquids that are attracted to magnets have been discovered, but these liquids are not preferred as the electrolytic solution 25 in the power storage device 3.

Next, the exterior body 10 of the power storage device 3 will be described. The exterior body 10 of the power storage device 3 needs to be non-magnetic. The results of investigation on whether or not materials of exterior bodies for a variety of power storage devices are attracted to magnets are shown in Table 2 below.

TABLE 2

| Material | Magnet test | |
|---|---|---|
| | Sheet shape | Can shape |
| SPCE | Very Bad | Very Bad |
| SUS304 | Good | Not Good |
| SUS316L | Good | Not Good |
| SUS329J4L | Bad | Bad |
| SUS430 | Very Bad | Very Bad |
| Non-magnetic stainless steel | Good | Good |
| Al | Good | — |
| Cu | Good | — |
| Ni | Very Bad | — |

In a method for testing the magnetic properties of the exterior bodies shown in Table 2, a specimen having a 0.2 mm-thick sheet shape and a specimen obtained by pressing the sheet to a can shape as the positive electrode can or the negative electrode can were respectively brought close to a magnet, and whether or not the specimens were attracted to the magnet was observed. Exterior bodies that were not attracted to the magnet were evaluated as 'Good', exterior bodies that were weakly attracted to the magnet were evaluated as 'Not Good', exterior bodies that were attracted to the magnet were evaluated as 'Bad', and exterior bodies that were strongly attracted to the magnet were evaluated as 'Very Bad'.

As shown in Table 2, cold-rolled steel sheets containing iron as a primary component (SPCE) or ferrite-based stainless steel (SUS430) were not strongly attracted to the magnet. Austenite-ferrite duplex stainless steel (SUS329J4L) was attracted to the magnet. Austenite-based stainless steel (SUS304, SUS316L) was not attracted to the magnet in the sheet shape, but austenite-based stainless steel pressed to a can shape was strongly attracted to the magnet. This is considered to be because, in the process of pressing the sheet, some of austenite was transformed to martensite which is magnetic. Non-magnetic stainless steel (NM17 manufactured by NAS Stainless Steel Strip Mfg. Co., Ltd.) was attracted to the magnet both in a sheet shape and in a can shape after being pressed. In addition, aluminum and copper were not attracted to the magnet. Nickel was strongly attracted to the magnet.

From the above-described test results, it is possible to select the active materials that are used for the positive electrode 21 and the negative electrode 22 on the basis of, for example, the results of the magnetic test shown in Table 1.

In a case in which a silver oxide battery (SR) is applied as the power storage device 3, it is possible to produce a non-magnetic power storage device 3 at a voltage of 1.5 V using $Ag_2O$ as a positive electrode active material and Zn as a negative electrode active material.

In a case in which a lithium secondary battery is applied as the power storage device 3, it is possible to produce a non-magnetic power storage device 3 at a voltage of 1.5 V using $Li_4Ti_5O_{12}$ as a positive electrode active material and a material obtained by reacting Li with SiO as a negative electrode active material.

In a case in which a lithium-ion secondary battery is employed as the power storage device 3, it is possible to produce a non-magnetic power storage device 3 at a voltage of 3.7 V using $LiCoO_2$ as a positive electrode active material and C as a negative electrode active material.

In a case in which an electric double layer capacitor is employed as the power storage device 3, it is possible to produce a non-magnetic power storage device 3 using activated carbon for the positive electrode 21 and the negative electrode 22.

In a case in which an alkaline dry battery, an alkaline battery (LR), a lithium primary battery (CR), a lithium secondary battery, or the like is applied as the power storage device 3, a Mn-based active material is used for the positive electrode 21. The Mn-based active material is strongly attracted to magnets, and thus it is desirable to dispose the Mn-based active material away from the actuator 4 that operates using an electromagnetic force.

A substance obtained by mixing an auxiliary conducive agent made of carbon and a resin binder with the above-described active material as necessary is compressed, thereby producing the positive electrode 21 and the negative electrode 22.

The separator 23 is formed of a material of a non-magnetic body such as polypropylene, polyethylene, polytetrafluoroethylene, or cellulose.

As the electrolytic solution 25, a mixture of any of the solvents and the electrolytes described above is used.

A material forming the exterior body 10 of the power storage device 3 can be selected from, for example, the results of the test shown in Table 2 in consideration of a method for working the exterior body 10. For example, in a case in which the exterior body 10 is formed without plastically deforming a metal sheet, the exterior body is preferably formed of any material of austenite-based stainless steel, non-magnetic stainless steel, aluminum, and copper. In a case in which the exterior body 10 is formed by means of plastic deformation through a press work or the like, the material is optimally non-magnetic stainless steel. Aluminum is non-magnetic, but is flexible and not easily stretchable, and thus the press work of aluminum is difficult. In addition, for the exterior body 10, it is necessary to take strength, weight, corrosion resistance, and the like into consideration. Aluminum is lightweight and has excellent corrosion resistance in the air or in non-aqueous electrolytic solutions, but has a defect of a low mechanical strength. Copper has a defect of being easily oxidized in the air. A variety of stainless steel has a sufficient mechanical strength and stable corrosion resistance in the air, but is inferior to aluminum in terms of the corrosion resistance in non-aqueous electrolytic solutions. In the present embodiment, the positive electrode can 11 and the negative electrode can 13 are formed by pressing a sheet material of non-magnetic stainless steel.

The gasket 12 is formed of a resin material which is a non-magnetic body having an insulation property such as nylon, polypropylene, polyphenylene sulfide, or polyether ether ketone.

The protective film 14 is formed of a material which is a non-magnetic body having a conductive property and is not easily corroded. Specifically speaking, the protective film 14 is formed of a material including at least one of carbon and aluminum. The protective film 14 is formed by, for example, applying paste obtained by mixing carbon powder, a resin, and a solvent to the inner surface of the positive electrode can 11 and drying the paste. In addition, the protective film 14 can also be formed by forming an aluminum film on the inner surface of the positive electrode can 11 by means of deposition, sputtering, or the like. Furthermore, the protective film 14 can also be formed by producing a clad sheet made up of a material that is not attracted to magnets such as non-magnetic stainless steel and aluminum and pressing the clad sheet to a can shape.

As described above, the most preferable aspect is that all of the members that are used in the power storage device 3 are formed of a material that is not attracted to magnets.

The actuator 4 is disposed between the power storage device 3 and the partition wall 2b in the second space S2. The actuator 4 includes a pipe 41, a magnet 43 disposed in the pipe 41, and a pair of coils 45 disposed at both end portions of the pipe 41. The pipe 41 is formed of, for example, aluminum in a cylindrical shape sealed in both end portions. The pipe 41 is concentrically disposed with the capsule 2. The magnet 43 is formed to be shorter than the length of the pipe 41 and is disposed so that the location thereof is variable in the axial direction in the pipe 41. The pair of coils 45 are respectively wound around the outer circumferential surfaces of both end portions of the pipe 41. The actuator 4 applies alternating current generated by the control circuit 8 to the coils 45, thereby reciprocally moving the magnet 43 which is an armature in the axial direction and causing the capsule endoscope 1 to advance in a certain direction with an inertial force generated by the movement of the armature or an impact force generated when the armature collides with an external wall.

The power-receiving coil 5 is disposed in the second space S2 on a side of the power storage device 3 opposite to the actuator 4. The power-receiving coil 5 is formed in a hollow shape. The power-receiving coil 5 is used for wireless power transmission together with an external power transmission coil not shown. Power received by the power-receiving coil 5 is supplied to the actuator 4, the camera 6, the LED 7, and the like through the control circuit 8 and also used to charge the power storage devices 3.

The camera 6 is attached to the partition wall 2b in the first space S1. The camera 6 is capable of capturing an image of the outside of the capsule 2 through the translucent one end portion 2a of the capsule 2.

The LED 7 is attached to the partition wall 2b in the first space S1. The LED 7 is capable of irradiating the outside of the capsule 2 through the translucent one end portion 2a of the capsule 2. Meanwhile, the LED 7 may be provided singly or a plurality of LEDs may be provided.

The control circuit 8 is disposed in the second space S2 between the actuator 4 and the circumferential wall of the capsule 2.

In the capsule endoscope 1 constituted as described above, power wirelessly transmitted to the power-receiving coil 5 from the external power transmission coil (not shown) is used to supply power to the actuator 4, the camera 6, the LED 7, and the like and charge the pair of power storage devices 3. When the capsule endoscope is constituted as described above, the amount of power being supplied to the actuator 4, the camera 6, the LED 7, and the like from the power storage devices 3 can be set to only an amount of power received which is decreased due to the variation of the location or angle of the capsule endoscope 1 with respect to the power transmission coil. Therefore, the capsule endoscope 1 can be operated using the small power storage device 3 having a smaller capacity compared with capsule endoscopes constituted to be operated only with power supplied from the power storage device 3. Meanwhile, as the power storage device 3, it is desirable to employ an electric double layer capacitor from which a larger electric current can be extracted instantly than primary batteries or secondary batteries.

Hereinafter, the action of the present embodiment will be described.

First, the evaluation results of the influence of the power storage device 3 on the actuator 4 will be described.

Figure 3:
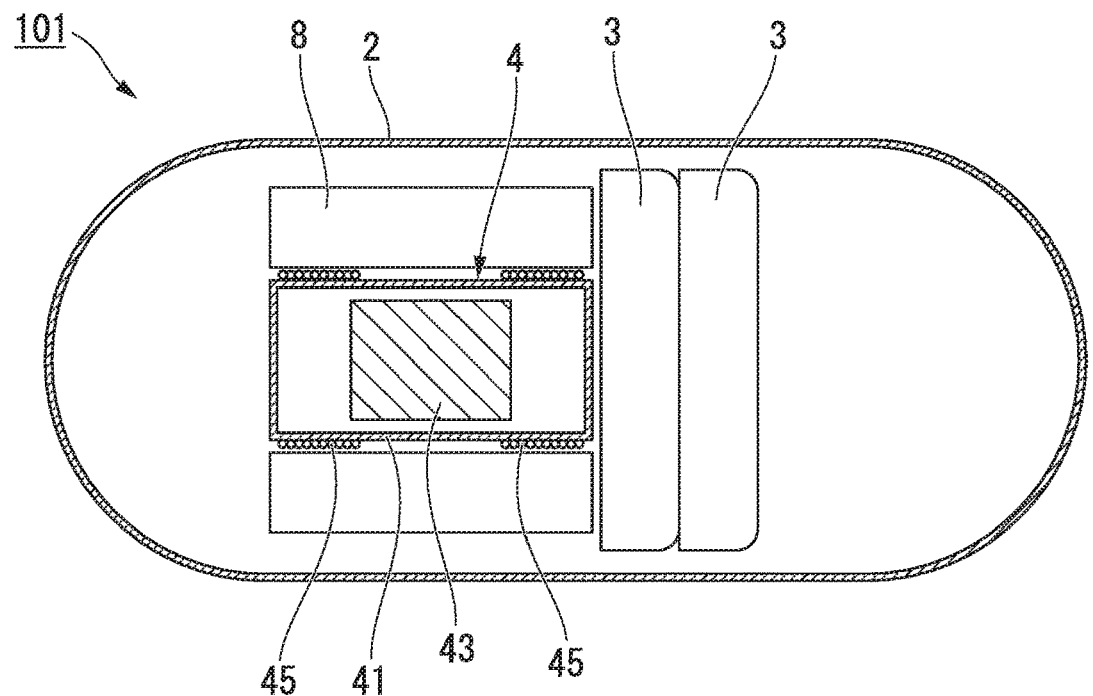
FIG. 3 is a cross-sectional view showing a schematic constitution of a capsule endoscope for evaluating an influence of the power storage device on an actuator.

FIG. 3 is a cross-sectional view showing the schematic constitution of a capsule endoscope 101 for evaluating the influence of the power storage device 3 on the actuator 4.

As shown in FIG. 3, the capsule endoscope 101 is constituted for evaluation and has the same constitution as the capsule endoscope 1 of the present embodiment except for the fact that the power-receiving coil 5, the camera 6, and the LED 7 are not provided.

In more detail, in the capsule endoscope 101, the power storage devices 3 are a coin-shaped electric double layer capacitor and have an outer diameter of 9.4 mm, and the thickness of each power storage device is 2.0 mm. The positive electrode can 11 and the negative electrode can 13 are formed by pressing a sheet material of non-magnetic stainless steel. The protective film 14 is formed by applying paste obtained by mixing carbon powder, a phenol resin, and a solvent to the inner surface of the positive electrode can 11 and drying the paste. The positive electrode 21 and the negative electrode 22 are formed by mixing activated carbon, carbon black, and polytetrafluoroethylene in a ratio of 7:2:1 (activated carbon:carbon black:polytetrafluoroethylene=7:2:1) and compressing the mixture. As the electrolytic solution 25, a solution obtained by dissolving 1 mol/L of tetraethylammonium fluoroborate in propylene carbonate was used.

When a samarium-cobalt magnet having a maximum energy product of 30 MGOe (239 kJ/m$^3$) was brought into contact with the surface of the power storage device 3 produced as described above, the power storage device 3 was not attracted to the magnet. A pair of the power storage devices 3 produced as described above were connected to each other in series, charged at 5 V, and then disposed side by side with the actuator 4, the magnet 43 which is the armature was horizontally moved, and the driving force for the capsule endoscope 101 was measured using a digital force gauge and found out to be 0.5 N.

In contrast, a power storage device constituted in the same manner as the power storage device 3 except for the fact that the positive electrode can 11 was formed of SUS329J4L, the negative electrode can 13 was formed of SUS304, and the protective film 14 was not provided (hereinafter, referred to as the "first power storage device for comparison") was produced. When the above-described samarium-cobalt magnet was brought into contact with the first power storage device for comparison, the first power storage device for comparison was attracted to the magnet. In a combination of the first power storage device for comparison and the actuator 4, it was not possible to reciprocally move the magnet 43 which was the armature, and it was not possible to cause the capsule endoscope 101 to travel.

From the above-described results, it is found that, according to the present embodiment, the power storage device 3 is formed of a non-magnetic body, and thus it is possible to suppress a magnetic field being varied by the disposition of the power storage device 3 close to the actuator 4 that operates using an electromagnetic force, and it is possible to prevent the operation of the actuator 4 from being hindered. Therefore, it is possible to ensure a sufficient driving force using the actuator 4, and it is possible to prevent an increase in the amount of power consumed by the actuator 4.

Next, the evaluation results of the influence of the power storage device 3 on the power-receiving coil 5 will be described.

Figure 4:
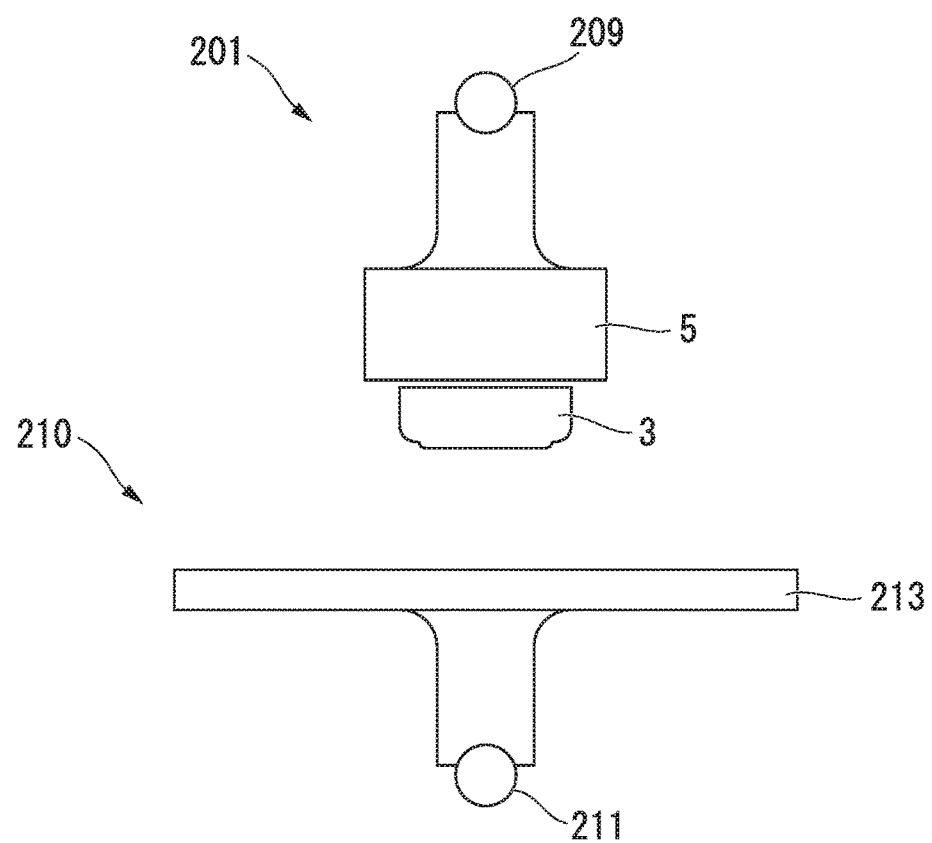
FIG. 4 is a schematic constitution view of a small electronic device and power transmission means for evaluating an influence of the power storage device on a power-receiving coil.
Figure 5:
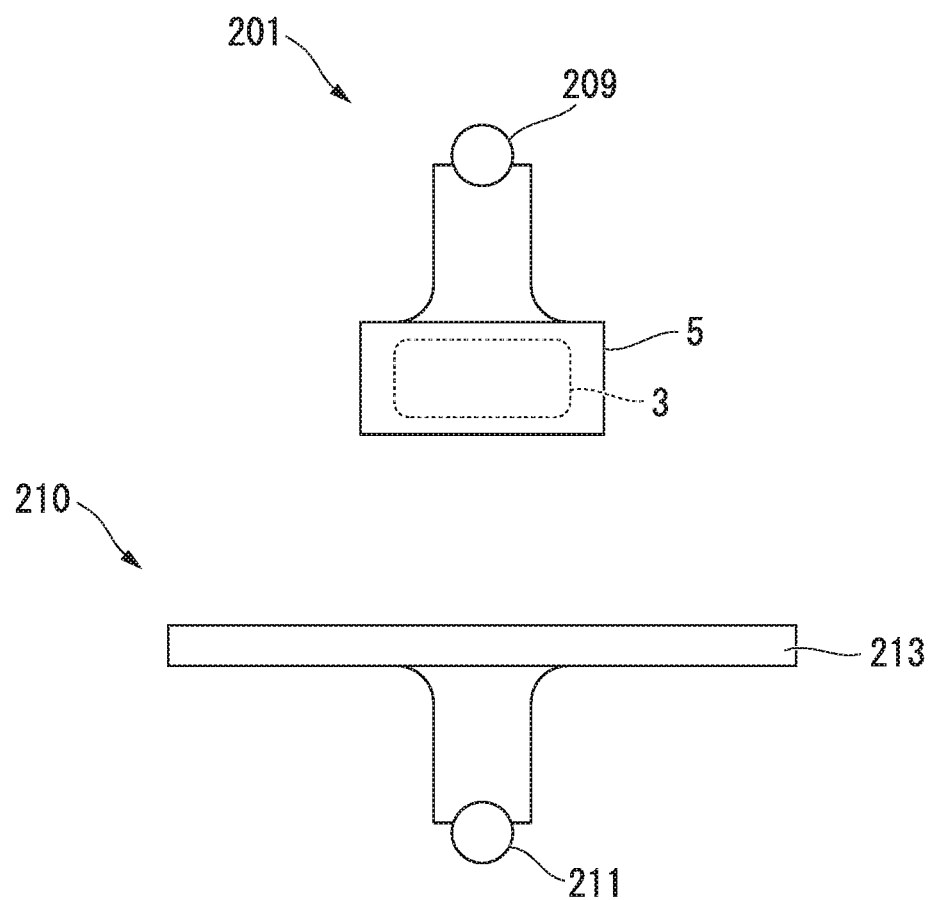
FIG. 5 is a schematic constitution view of the small electronic device and the power transmission means for evaluating the influence of the power storage device on the power-receiving coil.

FIG. 4 and FIG. 5 are schematic constitution views of a small electronic device 201 and power transmission means 210 for evaluating an influence of the power storage device 3 on the power-receiving coil 5.

As shown in FIG. 4, the small electronic device 201 includes the power-receiving coil 5 and a 150 mW electric light bulb 209 connected to the power-receiving coil 5. To the small electronic device 201, power is transmitted from the power transmission means 210. The power transmission means 210 includes an alternating current generator 211 and a power transmission coil 213 connected to the alternating current generator 211. The power transmission means 210 wirelessly transmits power from the power transmission coil 213 to the power-receiving coil 5.

First, when power was transmitted to the small electronic device 201 from the power transmission coil 213, the electric light bulb 209 was brightly lit. Furthermore, when power was transmitted to the small electronic device 201 from the power transmission coil 213 in a state in which the power storage devices 3 were disposed side by side with the power-receiving coil 5 between the small electronic device 201 and the power transmission coil 213, the brightness of the electric light bulb 209 was not changed, and the electric light bulb was brightly lit.

In contrast, when the power storage devices 3 were substituted with the first power storage devices for evaluation, the brightness of the electric light bulb 209 became dark.

From the above-described results, it is found that, according to the present embodiment, the power storage device 3 is formed of a non-magnetic body, and thus it is possible to suppress the amount of power received being decreased by the disposition of the power storage device 3 close to the power-receiving coil 5.

In addition, when the power storage devices 3 were disposed on the inside (inner portion) of the power-receiving coil 5 of the small electronic device 201 as shown in FIG. 5, similar to the state in which the power storage devices 3 were disposed side by side with the power-receiving coil 5, the electric light bulb 209 was brightly lit. As described above, even when the power storage devices 3 which are not attracted to magnets are fed into the hollow power-receiving coil 5, the amount of power received is not influenced, and thus it is possible to effectively use the space in the capsule 2. As the utilization of an empty space in the capsule 2 formed by the alteration in the disposition of the power storage devices 3, a greater driving force can be obtained by increasing the size of the actuator 4, a mechanism for collecting cells can be provided, or a mechanism which is mounted with medicine and capable of directly injecting the medicine into a diseased portion in a human body can be provided, and it is possible to produce the capsule endoscope 1 having higher performance.

Next, the evaluation results of the action of the protective film 14 will be described.

As a power storage device for comparison with the power storage device 3, a power storage device constituted in the same manner as the power storage device 3 except for the fact that the positive electrode can 11 and the negative electrode can 13 were formed of non-magnetic stainless steel, and the protective film 14 was not provided (hereinafter, referred to as the "second power storage device for comparison") was produced. The results of magnet tests and durability experiments of the power storage device 3 and the second power storage device for comparison are shown in Table 3 below.

TABLE 3

| | Protective film | Magnet test | Capacity retention (%) |
|---|---|---|---|
| Power storage device | Yes | Good | 92 |
| Second power storage device for comparison | No | Good | 0 |

In a method of the magnet test in Table 3, the power storage device 3 and the second power storage device for comparison were respectively brought close to a magnet, and whether or not the power storage devices were attracted to the magnet was observed. Power storage devices that were not attracted to the magnet were evaluated as 'Good', power storage devices that were weakly attracted to the magnet were evaluated as 'Not Good', power storage devices that were attracted to the magnet were evaluated as 'Bad', and power storage devices that were strongly attracted to the magnet were evaluated as 'Very Bad'. As a result, the power storage device 3 and the second power storage device for comparison were both not attracted to the magnet.

In the durability experiment, the capacity retention was measured in the following order.

(1) Capacity Measurement 1

The power storage device 3 and the second power storage device for comparison were respectively charged at 2.5 V and then discharged at a discharge current value per electrode area of 35 mA/cm$^2$, and a power storage capacity C1 was computed from a time taken for the charge voltage to reach 40% from 80%.

(2) The power storage device 3 and the second power storage device for comparison were fed into a constant temperature tank (40° C.) and continuously charged at a voltage of 2.5 V for one week.

(3) Capacity Measurement 2

A capacity C2 was computed using the same method as in Capacity Measurement 1.

(4) The capacity retention was set to C2/C1.

As shown in Table 3, the capacity retention of the second power storage device for comparison was 0%, whereas the capacity retention of the power storage device 3 was 92%.

From the above-described results, it is found that, since the protective film 14 was formed on the positive electrode can 11, it was possible to prevent the corrosion of the positive electrode can 11. Therefore, it is possible to produce an electric double layer capacitor in which the power storage devices 3 deteriorate only to a small extent.

As described above, according to the present embodiment, the power storage device 3 is formed of a non-magnetic body, and thus it is possible to suppress a magnetic field being varied by the disposition of the power storage device 3 close to the actuator 4 that operates using an electromagnetic force. Therefore, it is possible to prevent the operation of the actuator 4 from being hindered by the disposition of the power storage device 3 close to the actuator 4.

In addition, the power storage device 3 is formed of a non-magnetic body, and thus it is also possible to suppress a decrease in the amount of power received being decreased by the disposition of the power storage device 3 close to the power-receiving coil 5 for wireless power transmission.

Furthermore, in the capsule endoscope 1, the power storage devices 3 and the power-receiving coil 5 supply power to the actuator 4, the camera 6, the LED 7, and the like through the control circuit 8. Therefore, the amount of power being supplied to the actuator 4, the camera 6, the LED 7, and the like from the power storage devices 3 can be set to only an amount of power received which is decreased due to the variation of the location or angle of the capsule endoscope 1 with respect to the power transmission coil. Therefore, the capsule endoscope 1 can be operated using the small power storage device 3 having a small capacity.

In addition, the exterior body 10 of the power storage device 3 is formed of non-magnetic stainless steel, and thus it is possible to form the exterior body with a press work in an easier manner compared with a case in which the exterior body is formed of aluminum for which the press work is difficult, and it is possible to reduce the manufacturing cost. Therefore, it is possible to provide an inexpensive capsule endoscope 1.

In addition, in the exterior body 10, the protective film 14 formed of a material including at least one of carbon and aluminum is provided on the surface of the positive electrode can 11 which is in contact with the electrolytic solution 25 of the power storage device 3, and thus it is possible to prevent the exterior body 10 from being corroded by the contact between the exterior body 10 and the electrolytic solution 25. Therefore, it is possible to suppress the performance deterioration of the power storage device 3. Particularly, in the present embodiment, the exterior body 10 is formed of non-magnetic stainless steel, and thus the provision of the protective film 14 enables the reliable prevention of the corrosion of the non-magnetic stainless steel and the more effective suppression of the performance deterioration of the power storage device 3.

In addition, the electrodes (the positive electrode 21 and the negative electrode 22) of the power storage device 3 include at least one of silver oxide, manganese dioxide, lithium cobaltate, lithium manganate, lithium titanate, zinc, carbon, activated carbon, silicon, silicon monoxide, and lithium, and thus the capsule endoscope 1 including the power storage device 3 having a high electric capacity which is formed of a non-magnetic body can be obtained.

In addition, the power storage device 3 has a coin shape and thus can be stored in the cylindrical capsule 2 with no void. Therefore, it becomes possible to decrease the size of the capsule 2, and it is possible to further decrease the size of the capsule endoscope 1. In addition, it becomes possible to effectively use the limited space in the capsule 2, and it is possible to produce the capsule endoscope 1 having higher performance.

In addition, according to the capsule endoscope 1 of the present embodiment, it is possible to produce the capsule endoscope 1 which has a self-moving function, suppresses a decrease in the amount of power received caused by wireless power transmission, and has high performance, and it is possible to alleviate burdens on the bodies of patients.

Meanwhile, the present invention is not limited only to the embodiment described above with reference to the drawings, and a variety of modification examples can be considered within the technical scope thereof.

For example, in the above-described embodiment, the power storage device 3 has a coin shape, but the shape is not limited to the coin shape, and, for example, a cylindrical shape, a flat sheet shape, or the like as in dry batteries which is formed by the plastic deformation of a metal sheet with a press work or the like may also be employed.

In addition, in the above-described embodiment, in the capsule endoscope 1, the power storage devices 3 are disposed side by side with the power-receiving coil 5, but the disposition is not limited thereto. For example, in the capsule endoscope 1 shown in FIG. 1, the power storage devices 3 may be disposed inside the power-receiving coil 5 as shown in FIG. 5. According to this constitution, it is possible to effectively use the space in the capsule 2 and produce the capsule endoscope 1 having higher performance.

In addition, in the above-described embodiment, the capsule endoscope 1 includes the actuator 4 and the power-receiving coil 5, but the constitution is not limited thereto. The capsule endoscope 1 may employ a constitution in which the actuator 4 is provided, but the power-receiving coil 5 is not provided. In addition, the capsule endoscope may include the power-receiving coil 5, but not include the actuator 4.

In addition, in the power storage device 3 of the above-described embodiment, the protective film 14 is provided on all of the portion of the positive electrode can 11 which faces the storage space S, but the constitution is not limited thereto, and the protective film may be provided on a portion of a surface which faces the storage space S and is in contact with the electrolytic solution 25.

Additionally, it is possible to appropriately substitute constituent elements in the above-described embodiment with well-known constituent elements within the scope for the gist of the present invention.

INDUSTRIAL APPLICABILITY

According to the small electronic device of the present invention, it is possible to prevent the operation of the actuation component from being hindered by the disposition of the power storage device close to the actuation component. In addition, it is also possible to suppress a decrease in the amount of power received being decreased by the disposition of the power storage device close to the power-receiving coil for wireless power transmission. Therefore, the industrial applicability is significant.

REFERENCE SIGNS LIST

1 . . . CAPSULE ENDOSCOPE (SMALL ELECTRONIC DEVICE)
2 . . . CAPSULE (CASE)
3 . . . POWER STORAGE DEVICE
4 . . . ACTUATOR (ACTUATION COMPONENT)
5 . . . POWER-RECEIVING COIL
10 . . . EXTERIOR BODY
14 . . . PROTECTIVE FILM
21 . . . POSITIVE ELECTRODE (ELECTRODE)
22 . . . NEGATIVE ELECTRODE (ELECTRODE)
25 . . . ELECTROLYTIC SOLUTION

What is claimed is:
1. A small electronic device comprising:
an actuation component that operates using an electromagnetic force;
a power-receiving coil for wireless power transmission;
a power storage device having a positive electrode and a negative electrode; and
a case in which the actuation component, the power-receiving coil and the power storage device are stored,
wherein the power storage device is formed of a non-magnetic body and includes an exterior body formed of non-magnetic stainless steel,
wherein the exterior body includes a positive electrode can that is electrically connected to the positive electrode, and a negative electrode can that is electrically connected to the negative electrode, and wherein an inner surface of the positive electrode can includes: a first region having a protective film formed of a material including at least one of carbon and aluminum that directly contacts an electrolytic solution of the power storage device, and a second region that indirectly contacts the electrolytic solution located between the positive electrode can and the positive electrode.

2. The small electronic device according to claim 1, wherein the power storage device is disposed inside the power-receiving coil.

3. The small electronic device according to claim 1, wherein an electrode of the power storage device includes at least one of silver oxide, manganese dioxide, lithium cobaltate, lithium manganate, lithium titanate, zinc, carbon, activated carbon, silicon, silicon monoxide, and lithium as a material.

4. The small electronic device according to claim 1, wherein the power storage device has a coin shape.

5. The small electronic device according to claim 1, which is a capsule endoscope.

\* \* \* \* \*